United States Patent
Morikawa et al.

(10) Patent No.: US 8,271,076 B2
(45) Date of Patent: Sep. 18, 2012

(54) CORRECTION DEVICE TO BE INCORPORATED INTO BRAIN WAVE INTERFACE SYSTEM, ITS METHOD, AND COMPUTER PROGRAM

(75) Inventors: Koji Morikawa, Kyoto (JP); Shinobu Adachi, Osaka (JP)

(73) Assignee: Panasonic Corporation, Osaka (JP)

( * ) Notice: Subject to any disclaimer, the term of this patent is extended or adjusted under 35 U.S.C. 154(b) by 475 days.

(21) Appl. No.: 12/522,307

(22) PCT Filed: Oct. 28, 2008

(86) PCT No.: PCT/JP2008/003059
§ 371 (c)(1),
(2), (4) Date: Jul. 7, 2009

(87) PCT Pub. No.: WO2009/057278
PCT Pub. Date: May 7, 2009

(65) Prior Publication Data
US 2010/0106042 A1    Apr. 29, 2010

(30) Foreign Application Priority Data
Oct. 29, 2007 (JP) ................ 2007-280896

(51) Int. Cl.
*A61B 5/04* (2006.01)
(52) U.S. Cl. ................ 600/544; 600/545
(58) Field of Classification Search .......... 600/544, 600/545
See application file for complete search history.

(56) References Cited

U.S. PATENT DOCUMENTS
2005/0017870 A1 * 1/2005 Allison et al. ........... 340/825.19
(Continued)

FOREIGN PATENT DOCUMENTS
JP    61-184683    8/1986
(Continued)

OTHER PUBLICATIONS
International Preliminary Examination Report for corresponding Application No. PCT/JP2008/003059 dated Feb. 16, 2010 and partial English translation.

(Continued)

*Primary Examiner* — Michael Kahelin
*Assistant Examiner* — Tho Tran
(74) *Attorney, Agent, or Firm* — Renner, Otto, Boisselle & Sklar, LLP

(57) ABSTRACT

An option which is considered to be desired by a user is determined by using an electroencephalogram interface (IF), and a determination error for the option is detected based on an electroencephalogram. If a determination error is detected, the option is corrected based on the electroencephalogram information which was used for the option determination.

A correction apparatus to be incorporated in an electroencephalogram IF system is provided. The electroencephalogram IF system includes a biological signal measurement section, an analysis section for analyzing an event-related potential contained in an electroencephalogram signal of a user, an inference section for inferring an option desired by the user based on a result of analysis, and an output section for presenting the option inferred by the inference section to the user. The biological signal measurement section measures the electroencephalogram signal of the user based on a point of presenting the option to the user as a starting point. The correction apparatus includes: a determination section for determining correctness of the inferred option based on an event-related potential contained in an electroencephalogram signal acquired after inference of the option; and a correction section for, when the inferred option is determined to be incorrect, correcting the inferred option based on the event-related potential before inference of the option and designating a device operation based on the option after correction.

11 Claims, 10 Drawing Sheets

U.S. PATENT DOCUMENTS

2006/0101079 A1 5/2006 Morikawa et al.
2009/0062680 A1* 3/2009 Sandford ..................... 600/544
2009/0147148 A1 6/2009 Morikawa et al.

FOREIGN PATENT DOCUMENTS

| JP | 2004-157748 | 6/2004 |
| JP | 2004-275619 | 10/2004 |
| JP | 2005-034620 | 2/2005 |
| JP | 3786952 | 3/2006 |
| JP | 2007/066440 | 6/2007 |

OTHER PUBLICATIONS

Shin Seirishinrigaku (or "New Physiopsychology"), Published by Kitaoji Shobo, vol. 2, Sep. 20, 1997, p. 14-15 and a partial English translation.

International Search Report for corresponding application No. PCT/JP2008/003059 mailed Nov. 25, 2008.

Atsuko Sukenaka et al., "A Method of Question in Communication Aids based on Event Related brain Potentials"; IPSJ SIG Notes, vol. 96, No. 85, Sep. 12, 1996; pp. 17-24.

Emanuel Donchin et al.; "The Mental Prosthesis: Assessing the Speed of a P300-Based Brain-Computer Interface"; IEEE Transactions on Rehabilitation Engineering; vol. 8, No. 2, Jun. 2000, pp. 174-179.

Shin Seirishinrigaku (or "New Physiopsychology"), supervised by Hiroshi Miyata, vol. 2, p. 14.

Form PCT/ISA/237 and a partial English translation.

* cited by examiner

FIG.5
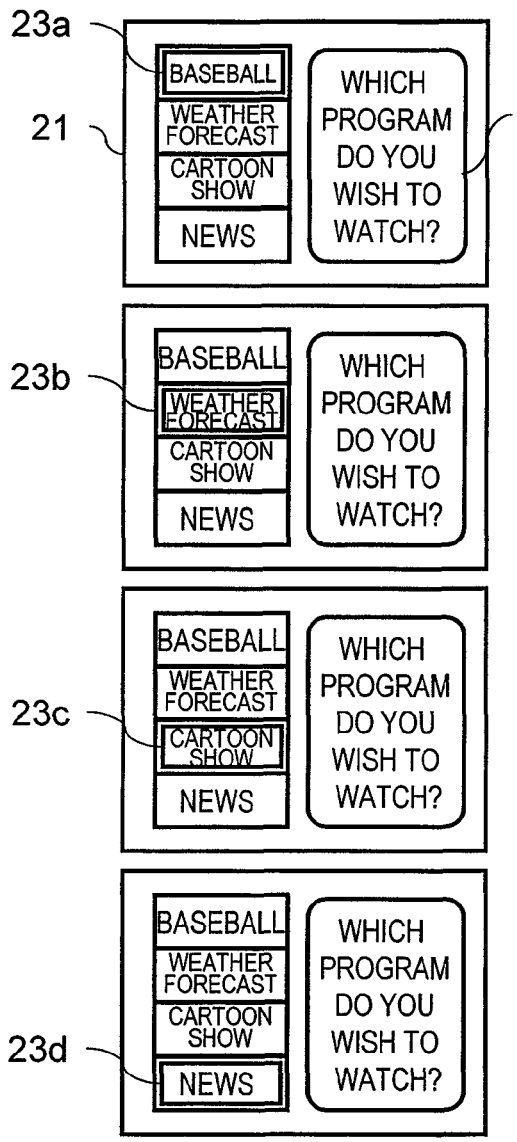
(a) MENU ITEM SCREEN
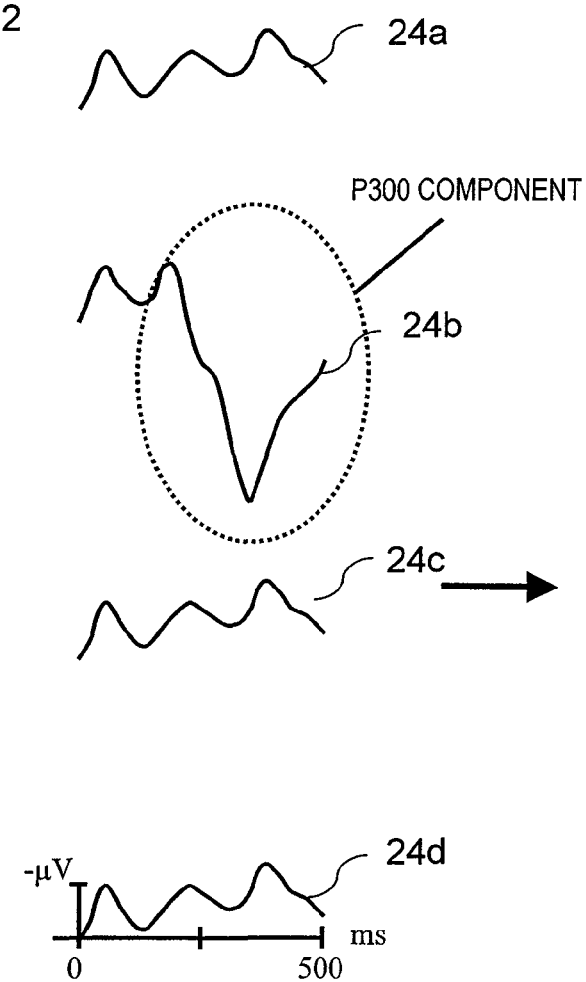
(b) EVENT-RELATED POTENTIAL BASED
ON SWITCHING OF MENU ITEM
AS A STARTING POINT (a) PRESENT SELECTION ITEMS (b) DESIGNATE SELECTION ITEM (c) DISPLAY INFERENCE RESULT

| AMPLITUDE RANK OF CORRECT OPTION | NUMBER OF TRIALS |
|---|---|
| FIRST | 69 |
| SECOND | 14 |
| THIRD | 7 |
| FOURTH | 6 |
| TOTAL | 96 |

WITHOUT CORRECTION: FIRST RANK ONLY = 72%
WITH CORRECTION: FIRST RANK + SECOND RANK = 87%

(a) WHAT IS THE RANK OF THE AMPLITUDE LEVEL OF CORRECT OPTION (b) PROPORTIONAL INDICATION

CORRECTION DEVICE TO BE INCORPORATED INTO BRAIN WAVE INTERFACE SYSTEM, ITS METHOD, AND COMPUTER PROGRAM

TECHNICAL FIELD

The present invention relates to a device having an interface for allowing a device manipulation to be performed by using an electroencephalogram. More specifically, it relates to a device and a method which are capable of, when a user's intent is to be distinguished by measuring an electroencephalogram in a device incorporating the aforementioned interface, automatically detecting if the device has made an incorrect distinction of the user's intent, and autonomously correcting the inference result, as well as a computer program to be executed in such a device.

BACKGROUND ART

Various devices have been proposed in our lives. While living among such devices, users enjoy desired information or services by manipulating the devices. Because of an increase in the number of devices themselves, an increase in the information that cannot be obtained without using devices, and so on, the importance of improving the manipulability of such interfaces is increasing year after year. In information devices (television sets, mobile phones, PDAs, etc.), for example, device manipulations are hitherto realized by selecting an manipulation option while watching a screen. As manipulation input means thereof, methods such as pressing a button, moving a cursor and making a confirmation, or manipulating a mouse while watching a screen have been used. However, it may have been impossible to execute a manipulation when both hands are unavailable, due to tasks other than device manipulations, e.g., household chores, rearing of children, and driving an automobile.

In answer thereto, there are input means utilizing biological signals from a user. Non-Patent Document 1 discloses a technique that utilizes an event-related potential of an electroencephalogram for distinguishing an option which a user wishes to select. Specifically, options are randomly highlighted, and the waveform of an event-related potential (often referred to as a P300 component) which appears about 300 milliseconds after a point in time that an option that the user wishes to select was highlighted is utilized to enable an inference of an option. According to this technique, even in a situation where both hands are full, or even in a situation where the user is unable to move his or her limbs due to an illness or the like, the user can select an option which they wish to select, whereby an interface for device manipulations, etc., can be realized. Also in Patent Document 1, an example of an electroencephalogram interface which similarly utilizes an event-related potential is described.

[Patent Document 1] Japanese Laid-Open Patent Publication No. 2004-275619

[Non-Patent Document 1] Donchin et al., "The Mental Prosthesis: Assessing the Speed of a P300-Based Brain-Computer Interface", IEEE TRANSACTIONS ON REHABILITATION ENGINEERING, Vol. 8, No. 2, June 2000

DISCLOSURE OF INVENTION

Problems to be Solved by the Invention

Since an electroencephalogram signal is a weak signal that has fluctuations, it is difficult to be rendered completely free of noises, and it does not always allow accurate distinction of a user's intent. For example, FIG. 3 of Non-Patent Document 1 shows that a 100% distinction rate cannot be attained with a small number of summations. According to reports, many distinction techniques in fact realize a distinction rate of about 80%-90% by using an arithmetic mean waveform from a plurality of times.

In such a situation, when an electroencephalogram interface is used, there is no guarantee that a device will make a correct distinction for every manipulation, meaning that, for example, one or two unsuccessful instances will be included for about every ten manipulations. Therefore, when an electroencephalogram interface is used, subsidiary options such as "Back" and "Cancel" are provided besides the actual options, in case the correct intent has not been successfully conveyed.

However, when subsidiary options are utilized, there is a trouble of having to go back by selecting such options for correction purposes with an electroencephalogram, and then again select the option that was meant to be selected. Therefore, studies for obtaining an improved distinction accuracy have been carried out.

An objective of the present invention is to, after an option which is considered to be desired by a user is determined through the use of an electroencephalogram interface (IF), detect a determination error for the option with an electroencephalogram, and if a determination error is detected, correct the option based on electroencephalogram information which was used for the option determination.

Means for Solving the Problems

A correction apparatus according to the present invention is to be incorporated in an electroencephalogram interface system. The electroencephalogram interface system includes: a biological signal measurement section for measuring and storing an electroencephalogram signal of a user, an analysis section for analyzing an event-related potential contained in the electroencephalogram signal, an inference section for inferring an option which is desired by the user based on a result of analysis by the electroencephalogram analysis section, and an output section for presenting the option inferred by the inference section to the user. The biological signal measurement section measures the electroencephalogram signal of the user based on a point of presenting the option to the user as a starting point. The correction apparatus comprises: a determination section for determining correctness of the inferred option based on an event-related potential contained in the electroencephalogram signal acquired after inference of the option; and a correction section for, when the inferred option is determined to be incorrect, correcting the inferred option based on the event-related potential stored before inference of the option, and designating a device operation based on the option after correction.

The determination section may determine correctness of the inferred option based on a positive waveform near 600 milliseconds of an event-related potential in the electroencephalogram signal acquired after inference of the option.

The determination section may retain a threshold value for determining correctness of the option; and the determination section may determine correctness of the inferred option based on whether or not a level of positive amplitude near 600 milliseconds of an event-related potential in the electroencephalogram signal acquired after inference of the option, equal to or greater than the threshold value.

The determination section may retain a threshold value for determining correctness of the option; and furthermore the determination section may change the threshold value in accordance with a difference in characteristic features near 300 milliseconds between an event-related potential which is measured corresponding to presentation of the inferred option and an event-related potential which is measured corresponding to presentation of another option, in the electroencephalogram signal acquired after inference of the option.

The determination section may change the predetermined threshold value in accordance with a difference in peak amplitude levels near 300 milliseconds between an event-related potential which is measured corresponding to presentation of the inferred option and an event-related potential which is measured corresponding to presentation of another option.

The determination section may retain a reference threshold value for determining the difference in peak amplitude levels; and the determination section may give a greater change in the threshold value for determining correctness of the option if the peak amplitude level is greater than the reference threshold value.

The correction section may correct the option by using an event-related potential which is acquired before inference of the option and measured corresponding to presentation of each option.

Before inference of the option, the output section may consecutively present a plurality of options; the biological signal measurement section may store an electroencephalogram signal of the user respectively measured based on the presentation of each option as a starting point; among the event-related potentials in the electroencephalogram signals corresponding to the respective options, the analysis section may infer an option corresponding to the event-related potential having a largest amplitude to be the option desired by the user; and as a correction candidate for the inferred option, the correction section may adopt an option corresponding to the event-related potential having a second largest amplitude, among the event-related potentials in the electroencephalogram signals corresponding to the respective options.

The correction section may not modify the inferred option if the determination section determines that the inferred option is correct.

A correction method according to the present invention is to be executed in an electroencephalogram interface system. The electroencephalogram interface system includes: a biological signal measurement section for measuring and storing an electroencephalogram signal of a user, an analysis section for analyzing an event-related potential contained in the electroencephalogram signal, an inference section for inferring an option which is desired by the user based on a result of analysis by the electroencephalogram analysis section, and an output section for presenting the option inferred by the inference section to the user. The biological signal measurement section measures the electroencephalogram signal of the user based on a point of presenting the option to the user as a starting point. The correction method comprises the steps of: determining correctness of the inferred option based on an event-related potential contained in the electroencephalogram signal acquired after inference of the option; when the inferred option is determined to be incorrect, correcting the inferred option based on the event-related potential stored before inference of the option; and designating a device operation based on the option after correction.

A computer program according to the present invention is to be executed in a correction apparatus incorporated in an electroencephalogram interface system. The electroencephalogram interface system includes: a biological signal measurement section for measuring and storing an electroencephalogram signal of a user, an analysis section for analyzing an event-related potential contained in the electroencephalogram signal, an inference section for inferring an option which is desired by the user based on a result of analysis by the electroencephalogram analysis section, and an output section for presenting the option inferred by the inference section to the user. The biological signal measurement section measures the electroencephalogram signal of the user based on a point of presenting the option to the user as a starting point. The computer program causes a computer of the correction apparatus to execute the steps of: determining correctness of the inferred option based on an event-related potential contained in the electroencephalogram signal acquired after inference of the option; when the inferred option is determined to be incorrect, correcting the inferred option based on the event-related potential stored before inference of the option; and designating a device operation based on the option after correction.

Effects of the Invention

With a correction apparatus according to the present invention to be incorporated in an electroencephalogram interface system, even if a device incorrectly determines an option that is desired by a user, the error is automatically corrected. This reduces the need to again perform a manipulation, thus allowing an electroencephalogram interface to be efficiently used.

BRIEF DESCRIPTION OF DRAWINGS

FIGS. 5(a) and (b) are diagrams showing an exemplary operation of an electroencephalogram interface.

Figure 1:
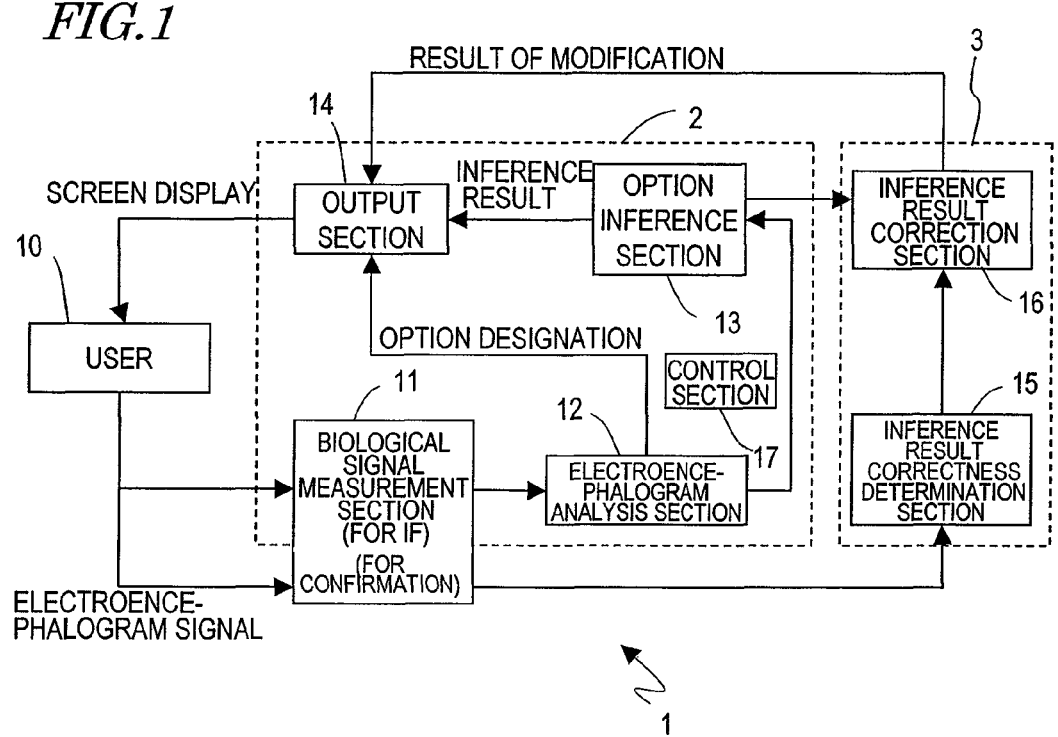
FIG. 1 A diagram showing the construction of an electroencephalogram interface (IF) system 1 according to Embodiment 1 which is used by a user 10.

DESCRIPTION OF REFERENCE NUMERALS 1 electroencephalogram interface system
2 electroencephalogram interface apparatus 3 correction apparatus
10 user
11 biological signal measurement section
12 electroencephalogram analysis section
13 option inference section
14 output section
15 inference result correctness determination section
16 inference result correction section
21 menu item screen
22 message box
23 option highlight
24 event-related potential
31 screen designating selection item
32 option highlight
33 screen displaying inference result
41 event-related potential (correct distinction)
42 event-related potential (incorrect distinction)

BEST MODE FOR CARRYING OUT THE INVENTION

Hereinafter, with reference to the attached drawings, embodiments of the electroencephalogram interface system according to the present invention will be described.

Prior to descriptions of the Embodiments, findings which have been obtained by the inventors will be described.

In a system where an option is inferred by utilizing an electroencephalogram, presumably, the possibility of determination errors being included concerning options desired by a user cannot be completely eliminated even if the inference accuracy is enhanced by improving the method of distinction. The inventors have paid attention to the response of a user when an incorrectly-determined option is presented. Specifically, the inventors have: performed a unique electroencephalogram experiment for identifying, based on an event-related potential of a user, any case where the device side has not been able to correctly infer the user's option; identified characteristic features of this event-related potential; and also found, through an electroencephalogram analysis, characteristic features of the waveforms of a correct option and an incorrectly inferred option when an incorrect inference is made. Based on these findings, an electroencephalogram interface which can automatically detect an incorrect inference and automatically correct an inference result at the device side has been realized. Hereinafter, as Embodiments 1 and 2, the electroencephalogram interface system will be described in detail.

Note that, in the present specification, a point in time after the lapse of a predetermined time since a certain point as calculated for acquiring an event-related potential is expressed as "about 300 milliseconds" or "near 600 milliseconds", for example. This means possible inclusion of a range around a specific point in time, such as "300 milliseconds" or "600 milliseconds". Generally speaking, it is known that there are 30 to 50 milliseconds of differences (shifts) in event-related potential waveform between individuals ("JISHOU-KANRENDENI (ERP) MANYUARU—P300 WO CHUSHINNI—(or "Event-Related Potential (ERP) Manual—mainly concerning P300—"), edited by Kimitaka KAGA et al., Shinohara Shuppan Shinsha, 1995, p. 30, Table 1). Therefore, the terms "about X milliseconds" and "near X milliseconds" mean that a breadth of "30 to 50 milliseconds" may exist before or after X milliseconds.

Embodiment 1

1. Construction of an Electroencephalogram Interface System and a Correction Apparatus FIG. 1 shows the construction of an electroencephalogram interface (IF) system 1 according to Embodiment 1 which is used by a user 10. The electroencephalogram IF system 1 includes an electroencephalogram interface (IF) apparatus 2 and a correction apparatus 3.

The electroencephalogram IF apparatus 2 is used for determining a user's intent based on an electroencephalogram, and causing a device to perform an operation that corresponds to the user's intent. The correction apparatus 3 is incorporated in the electroencephalogram IF system 1 in order to determine the correctness of the result by the electroencephalogram IF apparatus 2 of determining the intent of the user 10, and to correct the determination result.

The following is an outline of the operation of the electroencephalogram IF system 1. From among a plurality of options which are displayed on the screen of a display device, the electroencephalogram IF apparatus 2 determines an option which is considered to be desired by the user 10, by using an electroencephalogram of the user 10. The correction apparatus 3 determines whether that option is correct or not with an electroencephalogram of the user after the option is presented.

If it is detected that a waveform indicating incorrectness exists in the electroencephalogram of the user, the correction apparatus 3 corrects the option based on the electroencephalogram information which was used for the option determination. The result of correction is sent to the electroencephalogram IF apparatus 2, and the electroencephalogram IF apparatus 2 performs an operation that corresponds to the corrected option.

On the other hand, if it is detected that the option is correct based on the electroencephalogram of the user after an option is presented, the correction apparatus 3 does not perform any correction for the option. As a result, the electroencephalogram IF apparatus 2 performs an operation that corresponds to this option.

Hereinafter, the component elements of each of the electroencephalogram IF apparatus 2 and the correction apparatus 3 composing the electroencephalogram IF system 1 will be described.

The electroencephalogram IF apparatus 2 includes a biological signal measurement section 11, an electroencephalogram analysis section 12, an option inference section 13, an output section 14, and a control section 17.

The biological signal measurement section 11 is a device for measuring changes in the potential of an electrode which is worn on the head of the user 10, and may be an electroencephalograph, for example. The electroencephalogram analysis section 12 analyzes the electroencephalogram data which is detected by the biological signal detection section 11. Based on the result analyzed by the electroencephalogram analysis section 12, the option inference section 13 infers which option in an electroencephalogram interface the user is wanting to select. The output section 14 presents options to the user 10, presents a result of selection, or presents other information concerning device operations. If the device is a television set, for example, the output section 14 corresponds to a screen of the television set. In this case, television programs or the like are also output from the output section 14.

Next, the correction apparatus 3 includes an inference result correctness determination section 15 and an inference result correction section 16.

The inference result correctness determination section 15 (hereinafter referred to as the "determination section 15") acquires a response of the user 10 to the result of option inference which is presented by the output section 14, based on an electroencephalogram. Based on the acquired electroencephalogram, the determination section 15 determines the correctness of that inferred option.

If the determination section 15 determines that the result of option inference of the device is incorrect, the inference result correction section 16 (hereinafter referred to as the "correction section 16") again infers a result (option) which is considered to be correct, corrects the previous inference result, and returns it to the output section 14. If it is correct, no correction for the inference result is performed.

The control section 17 controls the operation of the entire electroencephalogram IF apparatus 2. The control section 17 is a semiconductor integrated circuit, for example.

Thus, the biological signal measurement section 11 is used for both the option inference in an electroencephalogram interface and the determination of a need of correction.

2. Specific Construction of the Electroencephalogram IF System

The inventors envisage that, in future, a brainwave IF system will be constructed in an environment in which a wearable-type electroencephalograph and a wearable-type display are combined. The user will always be wearing the electroencephalograph and the display, and be able to perform content viewing and screen manipulation by using the wearable-type display. Otherwise, it is envisaged that a brainwave IF system will be constructed in an environment (e.g., home) in which a home television set and a wearable-type electroencephalograph are combined. When watching television, the user is able to perform content viewing and screen manipulation by wearing the electroencephalograph.

Figure 2:
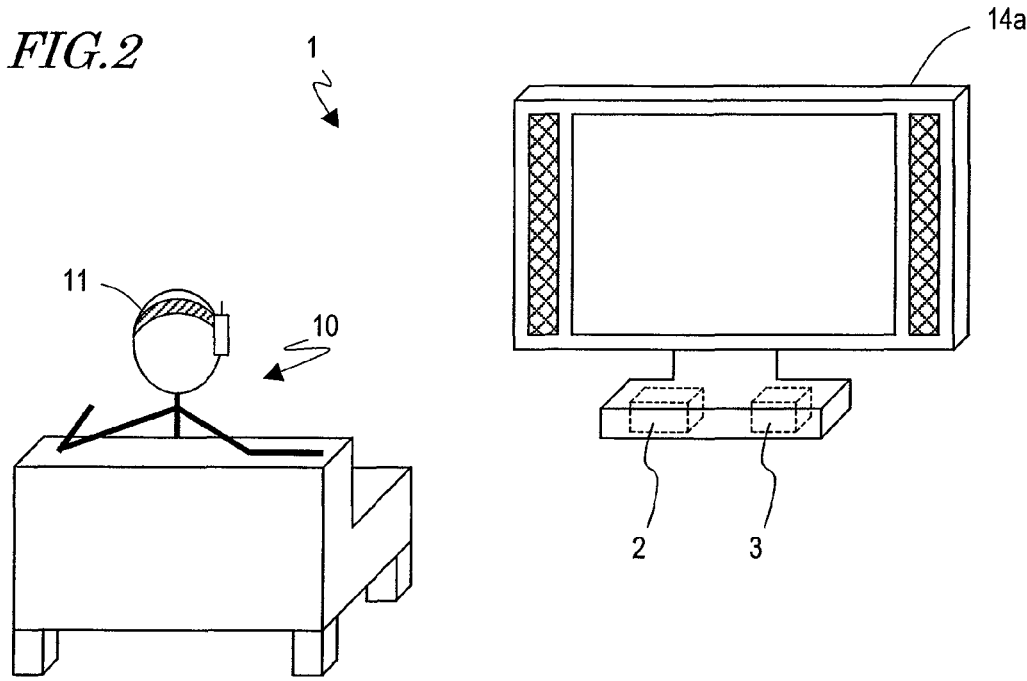
FIG. 2 A diagram showing a construction and an environment of use for the electroencephalogram IF system 1 as envisaged by the inventors.

For example, FIG. 2 illustrates a construction and an environment of use for the brainwave IF system 1 as envisaged by the inventors in the latter example. The brainwave IF system 1 is exemplified so as to correspond to a system construction of Embodiment 1 described later.

The brainwave IF system 1 is a system for providing an IF for manipulating a TV 14a by utilizing a brainwave signal from a user 10. A brainwave signal from the user 10 is acquired by the biological signal measurement section 11 which is worn on the head of the user, and transmitted to the electroencephalogram IF apparatus 2 in a wireless or wired manner. The electroencephalogram IF apparatus 2 internalized in the TV 14a recognizes an intent of the user by utilizing a P3 component of an event-related potential which constitutes a part of the brainwaves, and performs operations such as channel switching. While checking the operation of the electroencephalogram IF apparatus 2, the correction apparatus 3 performs a correction for the inferred option as necessary, thus performing a correction of the operation.

3. Outline of Processing by the Electroencephalogram IF System 1

Figure 3:
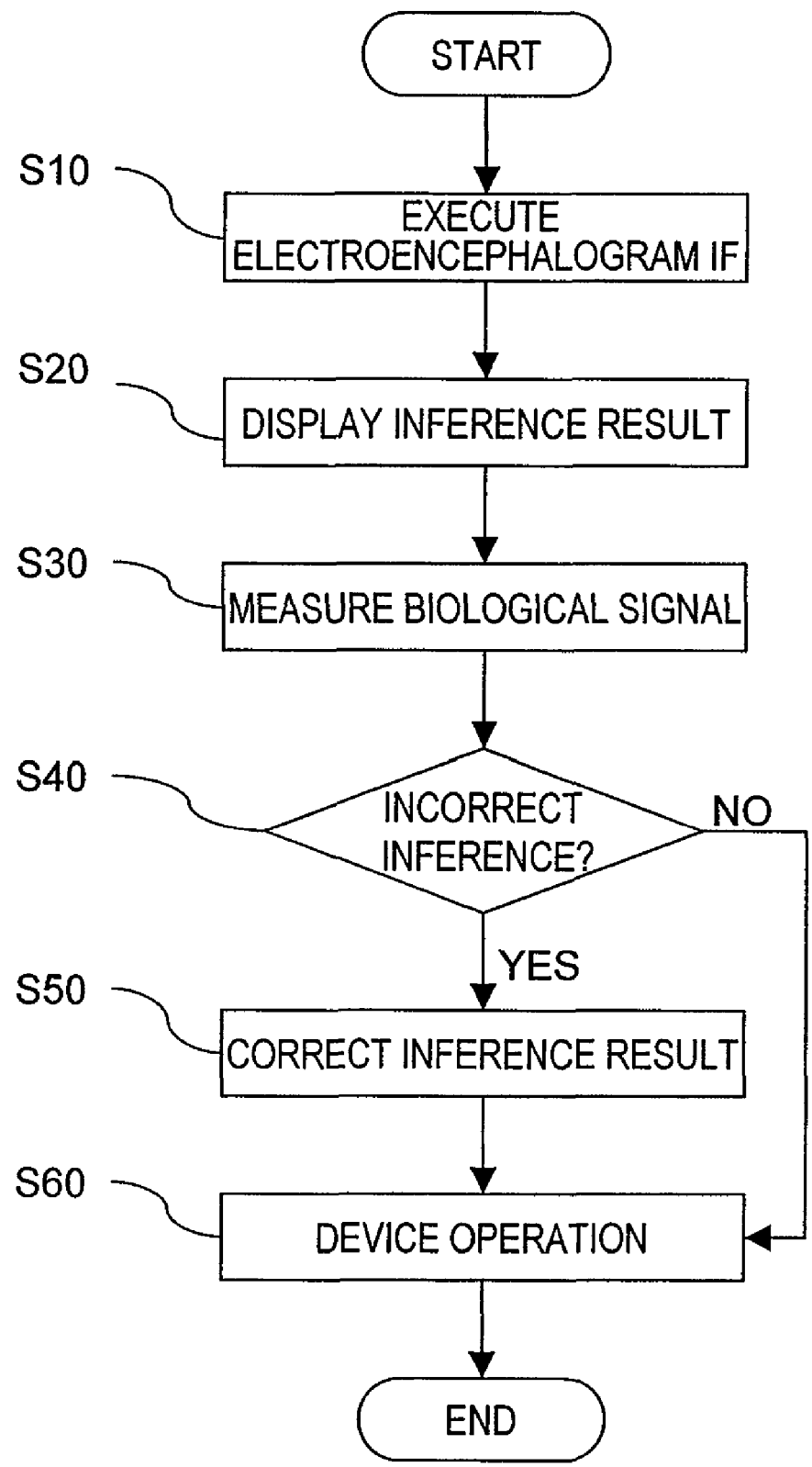
FIG. 3 A diagram mainly showing a procedure of processing by a correction apparatus 3.

Next, with reference to FIG. 3, the processing by the electroencephalogram IF system 1 including the correction process by the correction apparatus 3 will be described. FIG. 3 mainly shows a procedure of processing by the correction apparatus 3. After the processing by the electroencephalogram IF apparatus 2, the correction apparatus 3 determines whether the result of option inference by the electroencephalogram IF apparatus 2 is correct or not, and if it is incorrect, performs a correcting process.

At step S10, the electroencephalogram IF apparatus in FIG. 1 executes an electroencephalogram interface. Selectable options are presented on the output section 14 according to each scene, and a process of analyzing an event-related potential based on a point of highlighting each presented option as a starting point, and inferring the option which is intended by the user 10, is performed. The detailed operation of the electroencephalogram IF apparatus 2 will be separately described later with reference to a flowchart of FIG. 4. At step S10, the electroencephalogram IF apparatus 2 infers the option which the user 10 wants to select, and the result thereof is passed to the next step S20.

At step S20, the output section 14 presents the option having been inferred at step S10. As a result, the user 10 is able to confirm whether his or her intended option has been conveyed to the system or not. By performing the following process, the correction apparatus 3 is able to confirm whether the inferred option is correct or not.

At step S30, the biological signal measurement section 11 measures an event-related potential based on a point of displaying the inference result at step S20 as a starting point. This event-related potential contains information as to how the user 10 has felt with respect to the result of option inference being presented by the system. Specific descriptions of the waveform of the event-related potential will be given later.

At step S40, from the event-related potential measured at step S30, the determination section 15 of the correction apparatus 3 determines whether an inference that reflects the thought of the user 10 has been made or not. The determination of the correctness of the inference is made based on characteristic features of the electroencephalogram which have been identified through an experiment that was carried out by the inventors. If presence of an incorrect inference is determined, control proceeds to step S50; if absence of an incorrect inference is determined, control proceeds to step S60.

At step S50, based on the determination of an incorrect inference, the correction section 16 performs a process of correcting this inference result. Findings have been obtained also for the correction method through an analysis of the experimental results. An effective correction method will be described later.

At step S60, based on the inference result obtained at step S20 or on the result of correction of step S50, the output section 14 executes a device operation. For example, in the case of a task of changing a television program, this means that television program names or the like are presented as the options, and through a device operation of this step, a screen which is being displayed switches to a selected program name.

The correction apparatus 3 operates through the above processing. Hereinafter, the details of each of the above-described steps will be described.

4. Operation Outline and Processing Procedure of the Electroencephalogram Interface First, an operation of the electroencephalogram IF apparatus 2 which is performed at step S10 in FIG. 3 will be described.

Figure 4:
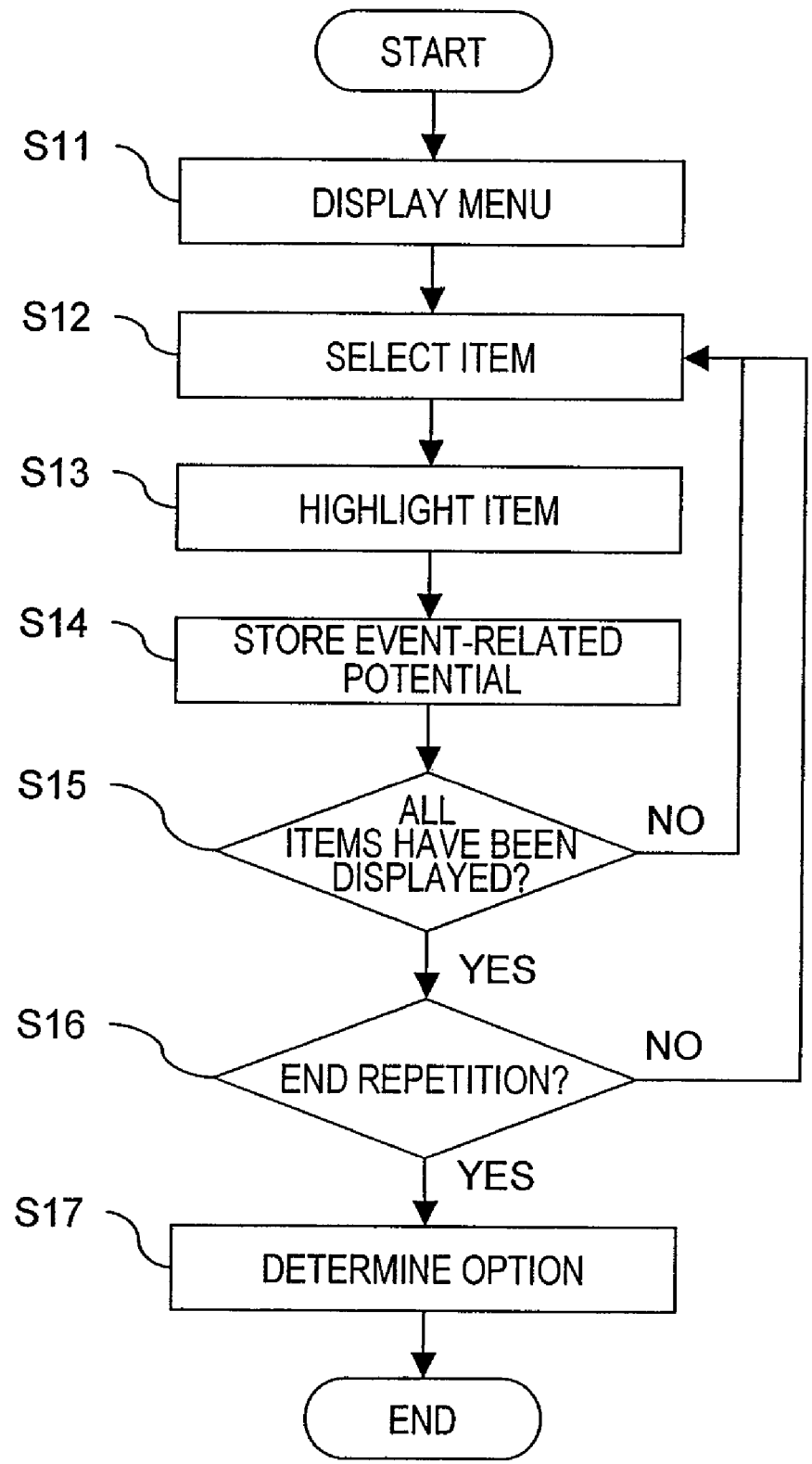
FIG. 4 Flowchart 1 of processing by the electroencephalogram IF apparatus.

By using an event-related potential, the electroencephalogram IF apparatus 2 distinguishes which item among a plurality of selection items being displayed on a display or the like the user wants to select. FIG. 4 shows a flowchart of processing by the electroencephalogram IF apparatus 2, and FIG. 5 shows an exemplary operation of an electroencephalogram interface.

Hereinafter, in accordance with the flowchart of FIG. 4, an operation of the electroencephalogram IF apparatus 2 will be described.

At step S11, the output section 14 displays a menu in which currently selectable options are listed. Once the electroencephalogram interface is activated, a menu screen 21 as shown in FIG. 5(a) is displayed. On the screen, a question 22 that says "Which program do you wish to watch?", and options 23 which are candidates of a program that may be being desired for watching, are presented. Herein, four are being displayed: "baseball" 23a, "weather forecast" 23b, "cartoon show" 23c, and "news" 23d. One of these four is highlighted in a bright color. For example, "baseball" 23a is highlighted in the screen 21.

At step S12, the control section 17 selects an item to be highlighted. In the example of FIG. 5(a), "baseball" 25a, which is the topmost, is selected. Then, every time this step S42 is executed, a next option is consecutively selected, until wrapping around to the topmost baseball after the fourth, i.e., news.

At step S13, the item selected at step S12 is highlighted by the output section 14. Highlight is an indication using a background which is brighter than any other item or an indication in a bright text color, or otherwise an indication via pointing with a cursor or the like. Herein, it suffices if, when the user 10 looks at it, it is clear which item the system is currently demanding attention to. In the electroencephalogram IF apparatus 2, at the time an option which he or she wants to select becomes highlighted, the user 10 focuses on the thought "I want to select it!", or simply focuses on the thought that it has been highlighted. This thought appears in the electroencephalogram, and is measured with an electroencephalograph at the next step.

At step S14, an event-related potential is acquired by the biological signal measurement section 11, and is stored to a memory (not shown) corresponding to each option. The event-related potential is acquired by the electroencephalograph of the biological signal detection section 11. The starting point for the event-related potential is set at the moment of highlighting at step S13, and an electroencephalogram from e.g. 200 milliseconds before and until 1 second after the moment is acquired. As a result, the user's response to the highlighted item is obtained. By storing it to a memory corresponding to each option, comparison in waveform between options, etc., becomes possible.

At step S15, the control section 17 determines whether all options have been displayed. If all options have been displayed, control proceeds to step S16, if not all options have been displayed, control returns to step S12, and the option to be next highlighted is determined.

At step S16, the control section 17 determines whether every option has been displayed a predetermined number of times or not. In an electroencephalogram interface, in the case where noise is often contained in each single waveform because of fluctuations the electroencephalogram waveform, a process of extracting a necessary signal through arithmetic mean is performed to solve this situation. This number of repetitions is set to 5 times or 10 times, for example, and each option is highlighted a plurality of times, and the responses thereof are summed to be used for signal distinction. This number of repetitions is determined based on the state of the electroencephalogram, the state of the individual's waveform, the determination accuracy, and the like; it may possibly be 1 time, without involving any summation.

At step S17, the option inference section 13 compares the event-related potentials for the highlighting of the respective options as stored at step S14, extracts a waveform that contains the most P300, and determines which option was meant to be selected. For example, in the example of FIG. 5(b), where the event-related potentials are 24a to 24d, it is only 24b that presents a characteristic waveform; therefore, "weather forecast" 23b, which is the option corresponding to the waveform 24b, is determined to be the option that the user 10 wanted to select. The method of comparison may be, for example, a technique of comparing the levels of peak amplitude near about 300 milliseconds, or a technique of generating a template from a typical P300 waveform and calculating a level of similarity with that template.

Through the above-described processing, it becomes possible to infer an option from an event-related potential.

Although step S12 is illustrated as selecting items consecutively, a method of random selection may also be possible. This will make it unknown which item is going to be selected in advance, thus leading to a possibility that the menu selection may be made more carefully.

Another method is also possible for the electroencephalogram interface processing. In the process of FIG. 4 (hereinafter referred to as Scheme 1), an option intended by the user is inferred by comparing the event-related potentials for the highlighting of all options. However, an intended option can also be inferred by processing each single event-related potential. Hereinafter, this processing method will be referred to as Scheme 2.

Figure 6:
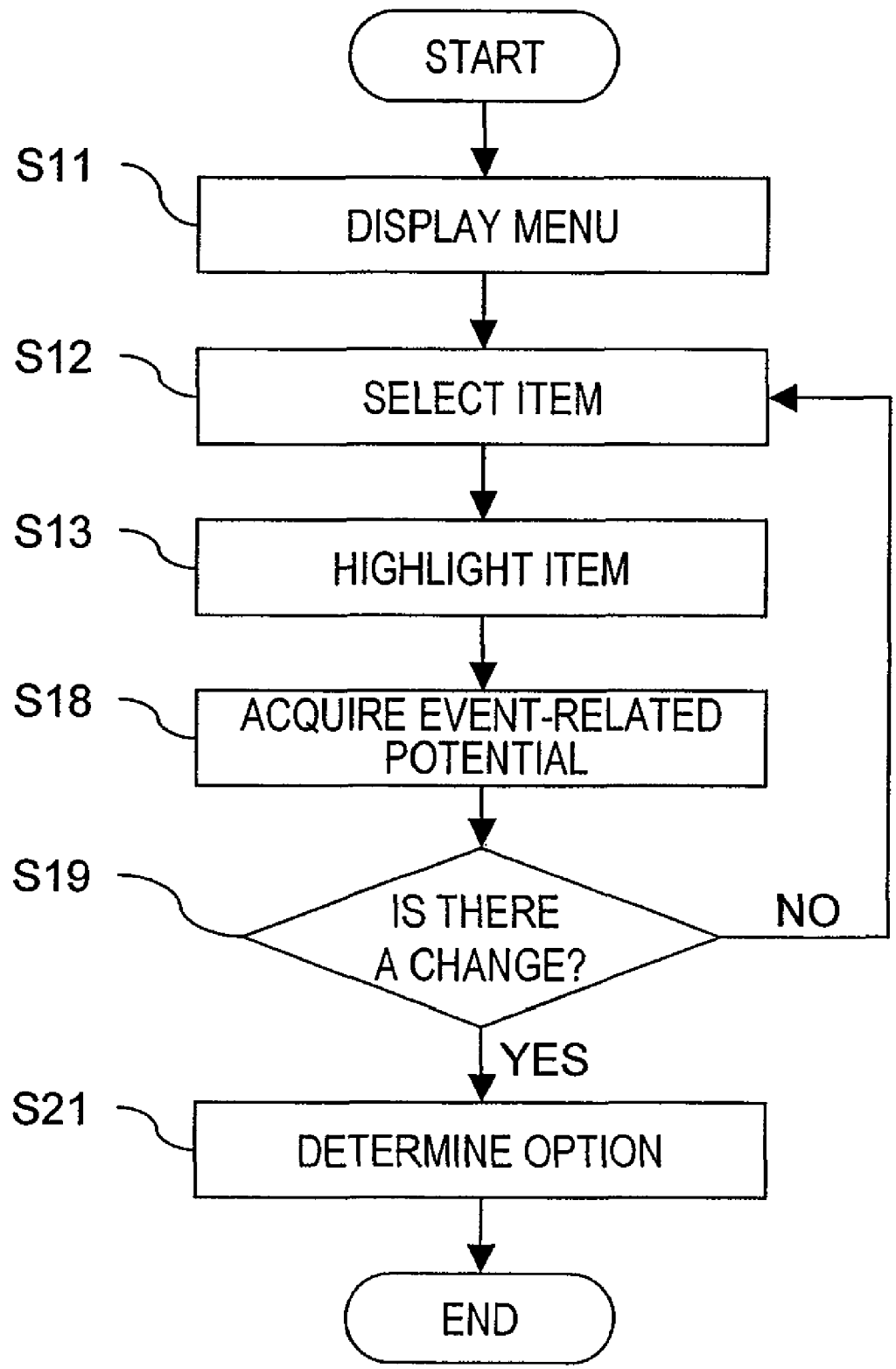
FIG. 6 Flowchart 2 of processing by the electroencephalogram IF apparatus.

FIG. 6 shows a flowchart of Scheme 2, which infers an option based on each single event-related potential. The same step number will be given to any process that is identical to a process shown in the flowchart of Scheme 1 in FIG. 4, and only the differences therefrom will be described.

From step S11 to step S13, similar processes to those of Scheme 1 in FIG. 4 are performed.

At step S18, the biological signal measurement section 11 acquires an event-related potential. Unlike Scheme 1 of FIG. 4, there is no need to perform a comparison between event-related potentials at the end, and therefore only the current waveform needs to be stored.

At step S19, the electroencephalogram analysis section 12 distinguishes the currently-acquired event-related potential with a method of distinction after distinction method adjustment. The distinction consists in distinguishing whether the waveform of the currently-acquired electroencephalogram is a waveform for an item which the user 10 wants to select, or a waveform for an item which the user does not want to select. FIG. 5(b) shows imaginary examples 24a to 24d of the electroencephalogram waveform. It is assumed that an electroencephalogram corresponding to the case where each menu item is highlighted is being displayed in FIG. 5(b). This illustrates that, in the case where the user 10 wants to watch "weather forecast" 23b, the characteristic waveform 24b is observed only when the item "weather forecast" 23b is highlighted. This is a component of the event-related potential called the P300 component, which is a positive characteristic waveform observed about 300 milliseconds after the menu item is switched. It is determined whether or not this component is observed. If this component is observed, control proceeds to step S21; if it is not observed, control returns to step S12.

At step S21, the option inference section 13 determines that the item for which a P300 component of the user 10 has been observed is the item which the user 10 wants to select, and thus an option is determined and passed to the next process.

Through such processing, without performing a button manipulation or the like, it is possible to select an intended option with an electroencephalogram.

5. Outline of an Experiment Performed by the Inventors

Next, with reference to FIG. 7, an experimental method and a data processing method performed by the inventors will be described. In addition, with reference to FIG. 8, exemplary screens to be presented to a test subject will be described. Through this experiment, it has become possible to identify characteristic features of an event-related potential for determining whether an inference result is correct or not.

Figure 7:
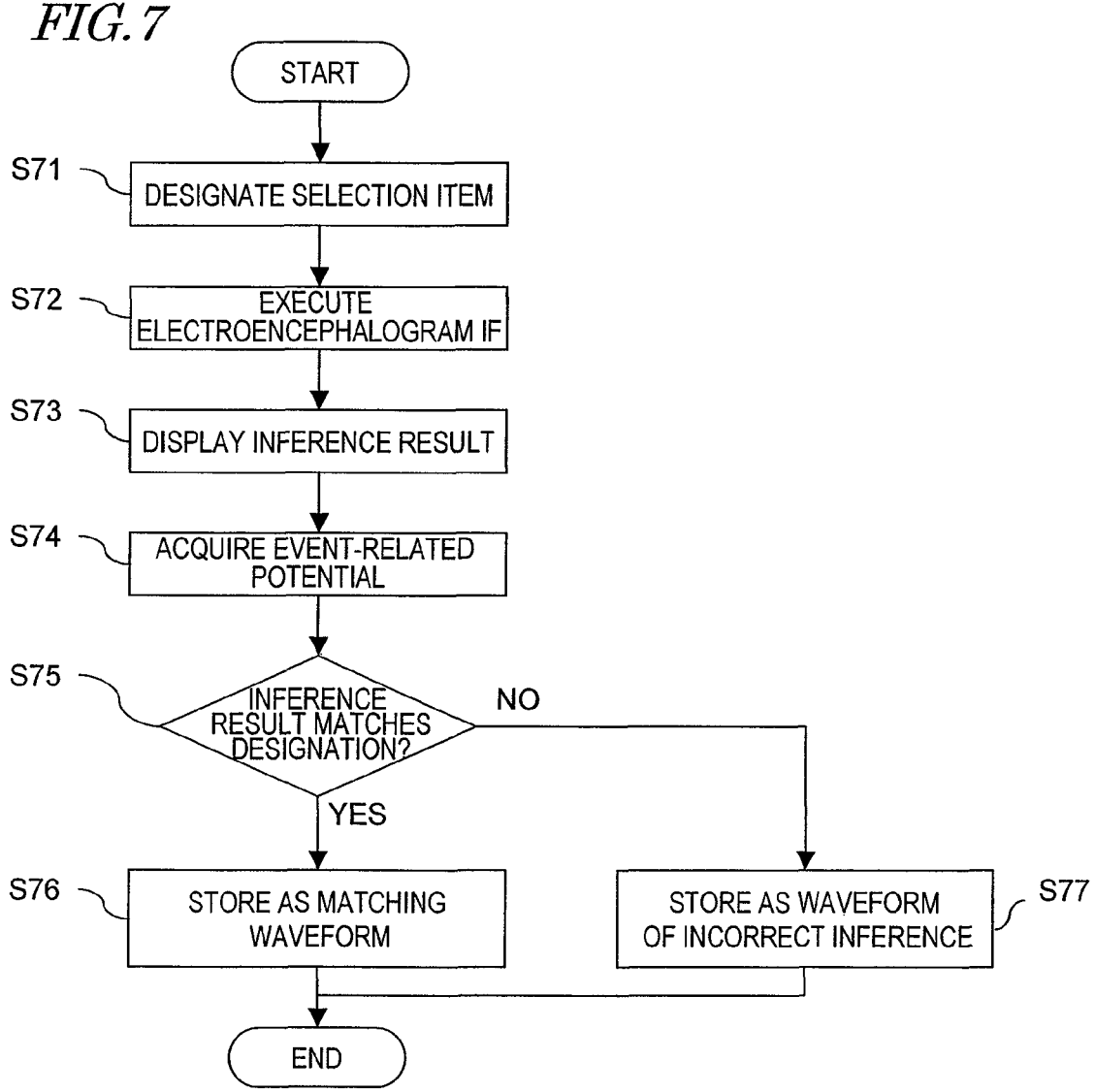
FIG. 7 A flowchart showing a procedure of processing concerning an experimental method and a data processing method of the inventors.
Figure 8:
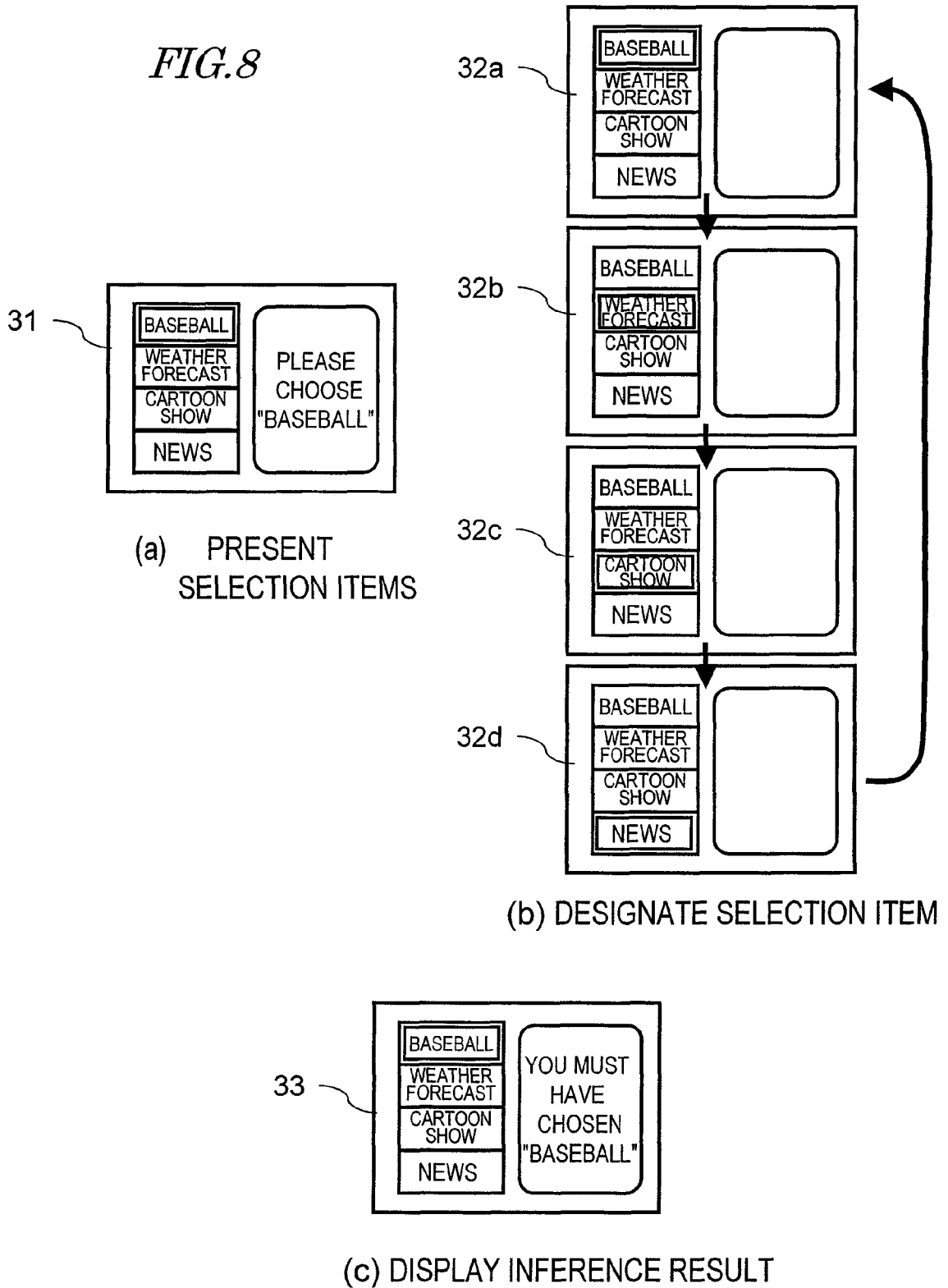
FIG. 8(a) to (c) are diagrams showing exemplary screens of an experiment concerning incorrect inference detection.

FIG. 7 shows a procedure of processing concerning the experimental method and the data processing method.

At step S71, an experiment program gives an instruction of a selection item to the user 10. Thus, the user 10 is asked to select a certain item in advance, this later serving an index as to whether an event-related potential of the user 10 has been correctly determined or not. FIG. 8(a) shows an example of the instruction of a selection item. An instruction such as "Please choose 'baseball'" 31 is shown on the screen, and the user selects the item according to the instruction.

At step S72 in FIG. 7, the electroencephalogram IF apparatus 2 activates an electroencephalogram interface. Specifically, through the process shown in FIG. 4, the electroencephalogram IF apparatus 2 determines whether P300 is contained in the event-related potentials when options 32a to 32d shown in FIG. 8(b) are presented to the user 10, and according to the result of determination, determines the option which the user 10 currently wants to select. The options are consecutively highlighted as in FIG. 8(b).

At step S73, as an inference result, a screen 33 of FIG. 8(c) is displayed, for example. The screen 33 displays "You must have chosen 'baseball'". This inference result is not related to the item which was designated at step S71, but is a result obtained through internal processing of the electroencephalogram in step S72. Therefore, it is not always the case that the inference result matches the instruction of step S71. A number of causes are possible for this: the electroencephalogram processing algorithm is one for a general purpose, and thus may make mistakes without being able to cope with individual differences; mixing of noise; an electroencephalogram was not well generated; or the like.

At step S74, an event-related potential is acquired based on the point of displaying the inference result at step S73 as a starting point. The range of acquisition may be—100 milliseconds to 1000 milliseconds from the starting point, for example. Out of this, the event-related potential from −100 milliseconds to 0 milliseconds is used for baseline correction. Note that the acquisition of an event-related potential is begun even before the starting point; this is technically possible without problems. For example, acquisition of the event-related potential may be allowed to start even before displaying the inference result, and the event-related potential after −100 milliseconds of the starting point may be adopted a posteriori. Otherwise, the timing of displaying an inference result on the screen is adjustable in advance, and therefore the timing of beginning acquisition of the event-related potential may be controlled to fall before it.

At step S75, it is determined whether the option which was designated to the user 10 at step S71 is identical to the option inferred by the system, which is displayed at step S73. If they match, control proceeds to step S76; if they match, control proceeds to step S77.

At step S76, the waveform data acquired at step S74 is stored as a waveform of the case where the user 10 has been able to correctly utilize the electroencephalogram interface. This event-related potential can be considered to contain information of the case where the user 10 has confirmed a feedback of his or her own expected result.

At step S77, the waveform data acquired at step S74 is stored as a waveform of the case where the user 10 has not been able to correctly utilize the electroencephalogram interface, or where the interface side has made an incorrect distinction. This event-related potential can be considered to contain information of the case where the user 10 encounters a feedback of a result which is different from his or her own expected result.

Through the process from step S71 to step S77, with respect to an instruction of a predetermined selection item, an event-related potential concerning whether the user 10 has been able to correctly manipulate an electroencephalogram interface, or whether the manipulation intent of the user 10 has been correctly conveyed to the electroencephalogram interface, can be acquired. By repeating this manipulation a predetermined number of times while changing the instruction of a selection item, the waveforms of the case where the user 10 has been correctly inferred and the waveforms of the case where the user 10 has not been correctly inferred can be collected. In the experiment, this process was performed for 12 test subjects.

Figure 9:
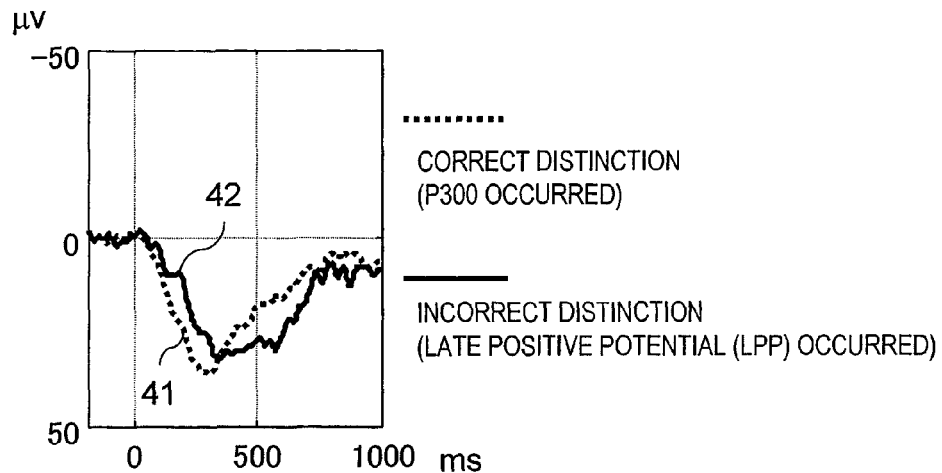
FIG. 9 A diagram showing two kinds of waveforms obtained by taking arithmetic means of event-related potential waveforms which were collected through the experimental procedure shown in FIG. 7.

FIG. 9 shows waveforms obtained by taking arithmetic means of the event-related potential waveforms which were collected through the experimental procedure shown in FIG. 7. The electroencephalogram was measured as changes in potential at Pz (the International 10-20 system) on the scalp, with reference to an earlobe. There were 12 test subjects, among whom only the data that contained instances of being incorrectly distinguished were collected. The vertical axis represents potential on the scalp, by the unit of μV, whereas the horizontal axis represents elapsed time since the point of displaying the inference result as a starting point, by the unit of milliseconds.

In FIG. 9, a dotted line 41 represents a waveform of the case where an option has been correctly selected and a correct distinction has been made. The waveform of this dotted line 41 has a reversed (positive) hill-shaped waveform centered around about 300 milliseconds, and this is considered to be the P300 waveform, which is supposed to be induced when a feedback that is as expected by the user is returned from the system.

On the other hand, the waveform of the solid line is a waveform in the case where an option which is different from the option expected by the user 10 is displayed. This red waveform has a relatively gentle, reversed (positive) hill-shaped waveform centered around about 400-600 milliseconds. This is considered to be a waveform that is induced in the case where an option which is different from the option intended by the user is returned from the system. This is a waveform having a positive component which is observed in a time slot later than that of P300. In the present specification, this waveform will be referred to as a "late positive potential" (LPP).

One signal resembling this late positive potential might be a signal having a positive component about 600 milliseconds after a point of feedback in Japanese Patent No. 3786952, "SERVICE PROVISION DEVICE, OUT-OF-EXPECTATION JUDGING DEVICE, AND OUT-OF-EXPECTATION JUDGING METHOD". The signal according to this patent is a signal which appears in the case where a feedback to one's own action is clearly not as expected, and a waveform having a relatively clear peak at about 550 to near 600 milliseconds is obtained.

It may be safely considered that a novel signal is being obtained through the present experiment according to the present invention. The reasons are that: since it is a measurement of a situation where an intent that was meant to be conveyed to a device fails to be correctly conveyed, the situation is different; and the characteristic features of the waveforms are different from each other. Moreover, in the aforementioned patent, P300 is not observed in the comparison of waveforms where an option as intended is successfully selected (as expected). Thus, it is a measurement of a different situation.

The following findings were newly obtained by summarizing the results of the experiment. Specifically, when a feedback which the user 10 has awaited is made, i.e., the system has correctly distinguished the electroencephalogram, P300 is observed. On the other hand, when a feedback which is different from what the user 10 has awaited is made, i.e., the system has incorrectly inferred the option, a late positive potential is observed.

By detecting the aforementioned signal, it can be determined whether the system has correctly inferred the option of the user 10 or not. For distinction of the signal, the time of the peak of the waveform of the reversed hill-shaped (latency) may be compared, or a difference in shape with respect to a template which is defined by a summed waveform of FIG. 8 may be checked; as a result, incorrect inferences by the system can be detected, and it becomes possible to know whether any modification of the inference result is necessary or not. More specifically, a distinction can be made based on whether the latency of the peak of the reversed hill-shaped waveform is closer to 600 milliseconds or 300 milliseconds. If it is closer to 600 milliseconds, a late positive potential is generated; and if it is closer to 300 milliseconds, it can be determined that P300 is being generated.

Moreover, since the hill-shaped waveform of the late positive potential is gentle, peak detection may be difficult; in this case, a summed waveform of the late positive potential and a summed waveform of P300 may both be utilized as templates, and a late positive potential may be detected based on closeness to either one of the templates.

Alternatively, when the two waveforms in FIG. 9 are compared, the potential is greater with P300 in any time slot earlier than about 450 milliseconds, whereas the potential (amplitude) is greater with the late positive potential in any time slot later than about 450 milliseconds. Thus, changes in potential may be utilized for distinction. For example, a zone average potential from 300 milliseconds to 450 milliseconds and a zone average potential of 450 milliseconds and 600 milliseconds may be compared, and if the former is greater, it may be determined that P300 has been generated; and if the latter is greater, it may be determined that a late positive potential has been generated, and so on.

6. Analysis of Data for Use in Correction

Figure 10:
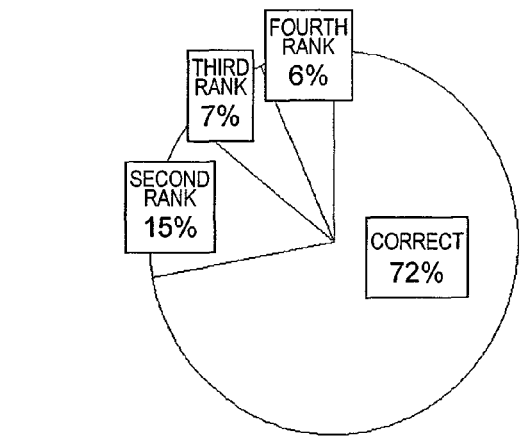
FIGS. 10(a) and (b) are diagrams showing an analysis result concerning correction.

Next, the correction method was studied. FIG. 10(a) shows a table obtained by, among the event-related potentials stored at step S14 in FIG. 4, analyzing for each trial an ordinal rank of the amplitude level of the correct option among all options, and counting it. This table indicates, when the electroencephalogram interface of step S72 in FIG. 7 is executed, an ordinal rank as to how large a P300 amplitude for the correct option is among all four event-related potentials (including the other options). For example, it indicates that the P300 amplitude when the correct option was presented took the largest value in 69 trials among all 96 trials, i.e., the P300 amplitude was greater than in the case where any other incorrect option was presented. It also indicates that it took the second largest value in 14 trials among all 96 trials.

In the electroencephalogram interface at step S72, among the four event-related potentials corresponding to the points of highlighting the respective options, the one whose P300 component or component at a point in time in that neighborhood has the largest amplitude is determined as the inferred option. In actuality, however, the waveform of the electroencephalogram will not always take the maximum amplitude among the four options, due to fluctuations, mixing of noise, and the like. This is illustrated in FIG. 10(a).

Selections of every 8 trials were made by 12 test subjects, and the data of the total 96 trials was analyzed. The P300 amplitude for the correct option proved the largest in 69 trials among these, thus accounting for 72% of the entirety. Therefore, when the maximum P300 amplitude is inferred to be the correct option, the correctness rate would be 72%.

Moreover, as shown in the table of FIG. 10(a), from the analysis results of the waveform amplitudes, there were 14 instances where the option which the user 10 wanted to select ranked the second among the four options, 7 instances where it ranked the third, and 6 instances where it ranked the fourth.

These results indicate that, even if the option of the case where the maximum amplitude is obtained is incorrect (27 times among 96 times in the table), the probability that the option of the second amplitude is correct is 14 times out of 27 times, i.e., 50% or more. This makes it clear that, if step S40 in FIG. 3 determines that the inference is incorrect, correction to an option of the second largest P300 amplitude will prove correct in more than half of the cases, among the event-related potentials for highlighting of the respective options when using an electroencephalogram interface. By utilizing this finding, a certain degree of correction would become possible.

FIG. 10(b) shows a result of studying the effect of correction based on the experiment data of FIG. 10(a). Among all 96 trials, the instances where a correct inference would have been made without an error are 69 times; thus, the correctness rate in the absence of an incorrect determination can be calculated to be 72%. On the other hand, when at least one correction (correcting to a candidate of the second largest amplitude) is introduced after an incorrect determination, 14 times out of the 27 times of errors will be properly corrected. In total, 83 times (=69 times+14 times) out of 96 times will prove correct, thus improving the overall correctness rate to 87%.

The reason why many instances thus concentrate among the top two ranks of P300 amplitude is that noise is considered to abruptly occur with some interval and exert an average influence during the presentation of all options. For example, changes in electro-oculographic potential due to blinking will influence the electroencephalogram as abrupt changes. In this case, an event-related potential corresponding to the correct option and event-related potentials influenced by the electro-oculographic potential are diversely present among the event-related potentials corresponding to the four options, and intermixing between the first and second ranks may have occurred in such a case. According to this view, even in the case where there are five or more options, the correct option will be included among the first and second ranks unless there is a continued mixing of noise, and thus this correction is believed effective. Although depending on the interval of highlighting (e.g., about 0.3 seconds to 1 second), approximately about 1 to 3 seconds is expected for one round of highlighting of options to be completed, and therefore not so many blinks will usually occur in this duration. Thus, this correction is considered to function effectively.

From such reasons, a large difference is considered to occur in the probability that the correct electroencephalogram will stray among the option of the second rank and the option of the third rank and after. Such characteristics apply not only to the case where the number of options is 4, but also to the case where it is 5 or more.

Now, a condition for the correct option to be the third rank or after will be considered. This will require a waveform similar to P300 to be observed in more than two options other than the correct option. Such a condition is not likely to occur with any source of noise that abruptly mixes in. Therefore, it can be considered that some other factor has caused the correct option to become the third rank or after.

For example, factors on the user side, e.g., the user's electroencephalogram not being generated at the timing of highlighting, or situations such as constant mixing of noise preventing the waveform from being stable are conceivable. In such cases, countermeasures against steady noises can be taken, e.g., filter improvements, improvement on the source power or the method of electrode attachment, whereby the possibility for the correct option to be included among the second rank or earlier can be enhanced.

In the present experiment, which illustrates results of an experiment that was performed for 12 test subjects, the determination method by the electroencephalogram IF apparatus 2 was a method of comparing a zone average potential from 200 milliseconds to 500 milliseconds. Although this method works relatively robustly for electroencephalogram waveforms of various shapes, it may not be seen as correctly determining P300 in some respects. It is considered that the initial correctness rate of 72% can be enhanced by improving the determination method. Performing optimization for the data of each individual will also be an effective method.

Such an improvement on the determination method will contribute to the removal of noise which is steadily mixed into a plurality of options, thus reducing the probability for the waveforms of the plurality of options to appear similar in waveforms to P300. Therefore, it is believed to increase the difference in probability between the case where the correct option is the second rank and the case where the correct option is the third rank or later, thus enhancing the effect of correction to the candidate of the second rank.

Moreover, when the initial correctness rate of 72% is improved, it is expectable that the detection accuracy of the incorrect inference detection step S40 will also be improved. It is known that the amplitude of an electroencephalogram increases for lower-frequency events (see, "SHIN SEIRISHINRIGAKU (or "New Physiopsychology"), supervised by Hiroshi MIYATA, vol. 2, P. 14). The amplitude of the late positive potential in the case where an inference result which is different from the intent of the user 10 is displayed is also considered to increase, thus presumably facilitating detection.

Therefore, by tuning the determination method, it is expected that the accuracy of detecting an incorrect determination will be improved, thus synergistically improving the overall accuracy.

It can be seen from the above that, from a characteristic electroencephalogram component of the user 10 at the time of an incorrect inference, it is possible to know at the device side whether a result of inference at the device side is incorrect or not, and there is further a possibility of automatic correction.

7. Detailed Procedures of the Incorrect Inference Detection Process and the Inference Result Correction Process Next, based on the experimental results obtained as above, the procedures of the incorrect inference detection process and the inference result correction process according to the present embodiment will be described in detail, with reference to FIG. 11 and FIG. 12. This process is executed after an inferred option is determined and indicated to the user.

Figure 11:
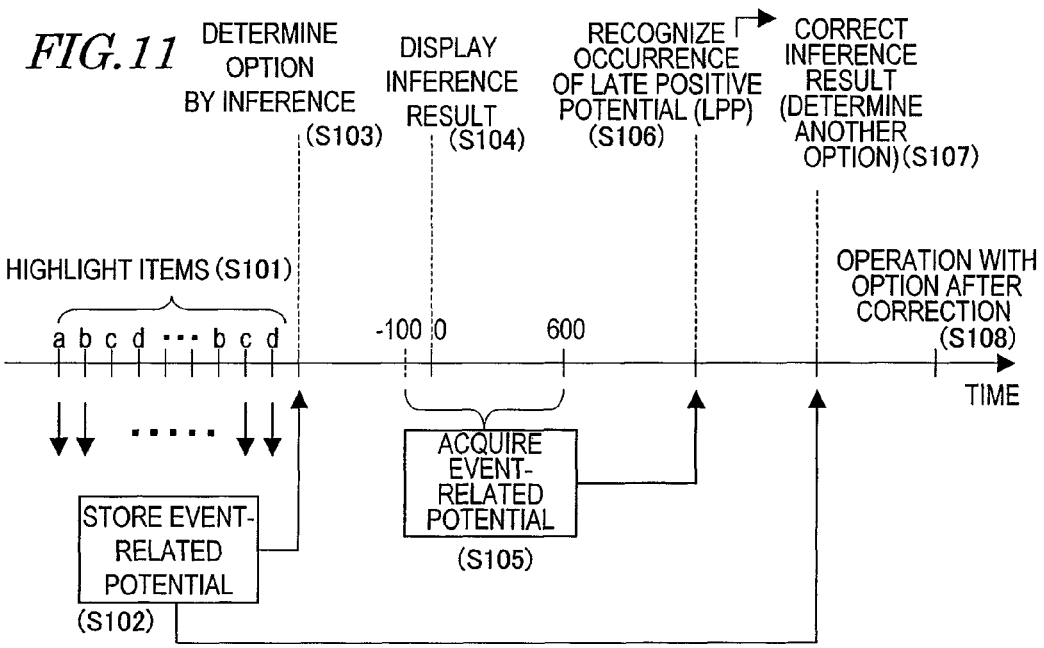
FIG. 11 A diagram showing the processing by an electroencephalogram IF apparatus 2 and a correction apparatus 3 according to Embodiment 1 in chronological order.

FIG. 11 shows the processing by the electroencephalogram IF apparatus 2 and the correction apparatus 3 according to the present embodiment in chronological order. The horizontal axis is a time axis, where time proceeds in the right direction. In FIG. 11, the content of each process is shown above the time axis. Hereinafter, the processing will be outlined along the time axis.

First, the control section 17 of the electroencephalogram IF apparatus 2 repeats selecting an item and highlighting it (FIG. 11, step S101). Each time doing so, it stores the event-related potential waveform (step S102). These processes correspond to steps S12 to S14 in FIG. 4.

When highlighting of the items is finished, the option inference section 13 of the electroencephalogram IF apparatus 2 infers and determines an option based on the stored event-related potential waveforms (step S103). This process corresponds to step S17 in FIG. 4.

Thereafter, the output section 14 displays the inference result (step S104).

After this, the correction apparatus 3 begins a process of determining whether this option is the option which is desired by the user or not.

The correction apparatus 3 acquires an event-related potential waveform in the range from e.g. −100 milliseconds to 600 milliseconds, based on a point of displaying the option inferred by the output section 14 as a starting point (step S105).

Then, the determination section 15 of the correction apparatus 3 determines whether or not the late positive potential described in FIG. 9 has occurred in the acquired event-related potential. If the determination section 15 recognizes occurrence of a late positive potential (step S106), it can be said that the option displayed on the output section 14 is incorrect. Thus, the correction section 16 executes a process of correcting the inferred option, and determines another option (step S107). At this time, the stored event-related potentials which were utilized when determining the first option are utilized as a basis for determining the other option.

The correction section 16 extracts the event-related potentials which were stored during item highlighting, and selects as the next candidate an option which was presented when the P300 amplitude of the event-related potential was the second largest.

The correction section 16 passes this option to the electroencephalogram IF apparatus 2 as a result of correction, and the output section 14 presents this option. The electroencephalogram IF apparatus 2 causes a device to execute an operation corresponding to this option (step S108).

Figure 12:
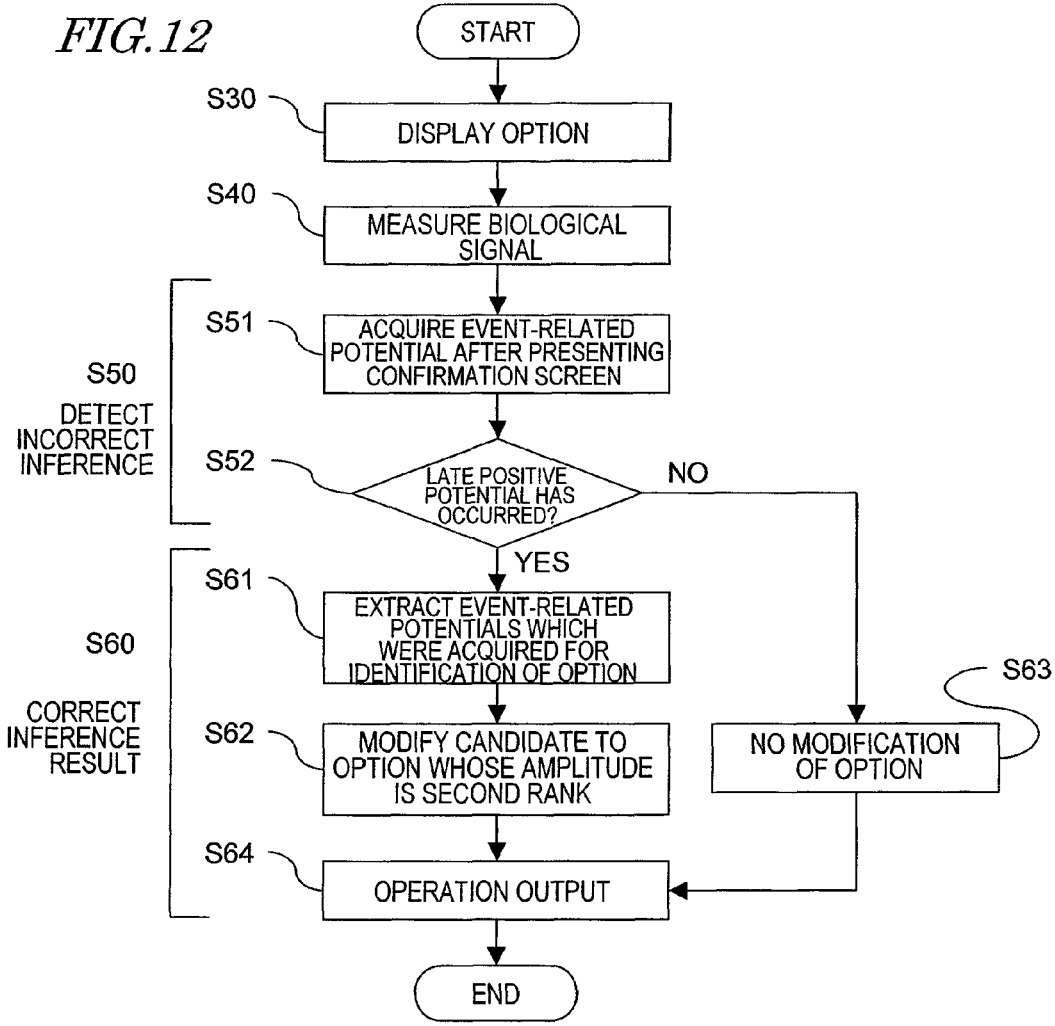
FIG. 12 A flowchart showing procedures of an incorrect inference detection process and an inference result correction process according to Embodiment 1.

Hereinafter, the procedure of processing will be described with reference to FIG. 12. FIG. 12 shows procedures of the incorrect inference detection process and the inference result correction process according to the present embodiment. It is assumed that item highlighting has previously been performed, and an option has been inferred and identified as indicating the user's intent.

At step S30, the output section 14 displays the inferred option.

At step S40, the biological signal measurement section 11 measures an electroencephalogram (event-related potential) for confirmation of the inference result. As is clear from FIG. 11, this measurement is not an event-related potential measurement that was performed for highlighting of an option.

At step S51, the biological signal measurement section 11 cuts out an the event-related potential based on the point of displaying at step S30 as a starting point. The range to be cut out is e.g. −100 milliseconds to 600 milliseconds. With this range, the response time of the electroencephalogram IF system 1 can be kept short. However, in the case where the response time may be more relaxed, it may be −100 milliseconds to 1000 milliseconds or the like, for example. This interval is to be determined based on a tradeoff between the response time and the detection accuracy required for the system.

At step S52, the determination section 15 determines whether a late positive potential is contained in the event-related potential which was cut out at step S51. The determination of the late positive potential can be made by using the shape of the waveform, near what milliseconds the peak latency is, and so on. Moreover, standard waveform templates of the P300 and late positive potential may be created, and it may be calculated which template the current waveform is closer to. If it is determined that a late positive potential is contained, control proceeds to step S61, where correction of the inferred option is performed. On the other hand, if it is determined that no late positive potential is contained, it means that the inference is correct. The process proceeds to step S63.

At step S61, for correction of the inferred option, the correction section 16 extracts from the memory an event-related potential for the highlighting of each option that was stored at step S14 in FIG. 4. Depending on the number of repetitions at step S16, each event-related potential may or may not have been subjected to arithmetic mean.

At step S62, from among the waveforms for the highlighting of the respective options extracted at step S61, the correction section 16 chooses as a correction candidate the option whose amplitude is the second rank. This makes it possible to utilize the finding that, when the first rank is incorrect, there is a probability of a half or more that the option of the second rank is correct.

At step S63, since there is no correction of the option, the correction section 16 sends to the electroencephalogram IF apparatus 2 a signal indicating that correction for the option is not to be performed. As a result, the option determined at step S30 is sent from the electroencephalogram analysis section 12 to the output section 14 as a final option. Thereafter, the process proceeds to step S64.

At step S64, since the final option to be executed by the device has been determined, the output section 14 causes the device to execute an operation. For example, in the case of selection of a television program as in the present embodiment, it instructs the television set to switch to and display the selected program.

Through such processing, even if the device makes an incorrect inference due to fluctuations of the electroencephalogram or mixing of noises, or the like, it is possible to correct that option, thus reducing the number of instances of re-manipulation, whereby the manipulability of the electroencephalogram interface is improved.

With the above construction, a user's intent can be more accurately conveyed by using an electroencephalogram signal not only for the inference of an option in an electroencephalogram interface, but also for the distinction of the correctness of the result of inferring the option, whereby an efficient use of an electroencephalogram interface is realized.

Embodiment 2

Embodiment 1 has illustrated an operation of the entire correction apparatus.

The present embodiment will describe an example where it is further possible to adjust the detection accuracy of incorrect inference by using an electroencephalogram during the operation of the electroencephalogram IF apparatus 2.

The inventors paid attention to the following points. That is, when executing an electroencephalogram interface, as shown in FIG. 5(b), various waveforms are observed with respect to the highlighting of each option. Based on the status of such waveforms, it can be determined how clearly the intent of the user 10 to make a selection has been conveyed to a device. It is possible to adjust the method of incorrect inference detection depending on the result of this determination.

Hereinafter, with reference to FIG. 13, a process of adjusting a threshold value for the late positive potential determination depending on the reliability of P300 in the electroencephalogram IF apparatus 2 will be described.

Figure 13:
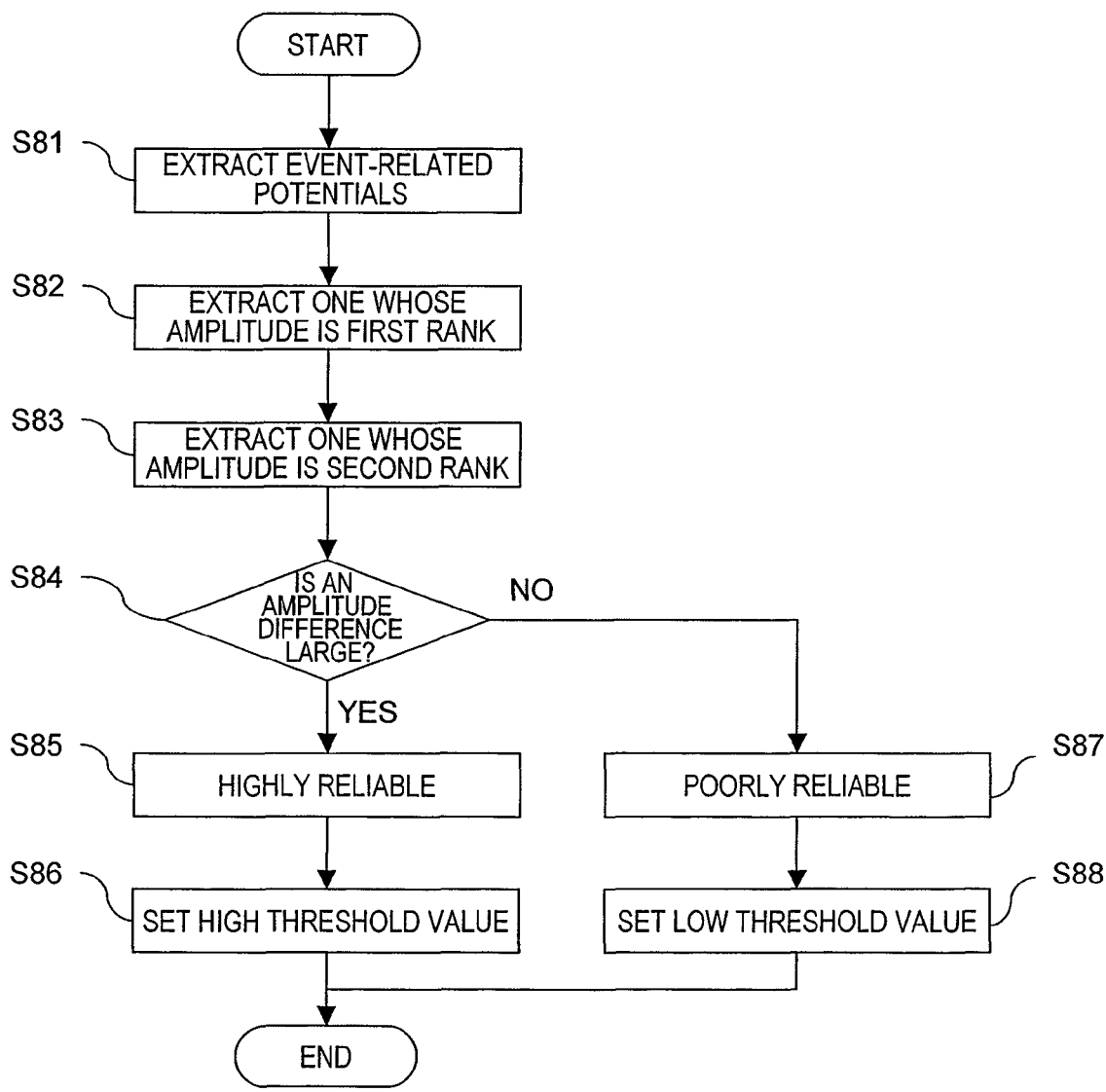
FIG. 13 A flowchart showing a procedure of a method of adjusting a threshold value for determining a late positive potential according to Embodiment 2.

FIG. 13 shows a procedure of the method of adjusting the threshold value for determining a late positive potential according to the present embodiment. This process is executed as a part of the incorrect inference detection process which is performed in the determination section 15.

At step S81, in order to refer to the waveform when executing an electroencephalogram interface, the determination section 15 extracts from the memory an event-related potential for the highlighting of each option that was stored at step S14 in FIG. 4. Depending on the number of repetitions at step S16, each event-related potential may or may not have been subjected to arithmetic mean.

At step S82, from among the waveforms extracted at step S81, the determination section 15 chooses one that has the largest P300 amplitude. The method of amplitude calculation may be, for example, extracting a hill-shaped waveform and using the amplitude of the highest point thereof in a zone from 200 milliseconds to 400 milliseconds.

At step S83, from among the waveforms extracted at step S83, the determination section 15 chooses one that has the second largest P300 amplitude.

At step S84, the difference between the two amplitudes extracted at steps S82 and S83 is detected. If the difference is greater than the threshold value, control proceeds to step S84; if it is smaller than the threshold value, control proceeds to step S87. The difference in amplitude is usable as an index as to how distant the candidate of the user's option having the largest amplitude is from the other options, i.e., how clearly the P300 waveform is being observed in only the option that is being desired to be selected.

An electroencephalogram has a lot of fluctuations, and is susceptible to noise influences. Therefore, when a shape which is similar to P300 accidentally occurs under noise influences, an event-related potential containing true P300 and an event-related potential containing the shape which is similar to P300 will both be observed, and it is expected that the difference in amplitude between the first rank and the second rank will be small. In this case, the possibility for the second rank to be correct is also considered as high.

An experimentally appropriate value can be determined for the amplitude difference. However, several μ V, and more specifically 2 μV or the like, can presumably be used as the size of the difference, for example. Without depending on the absolute value of the difference, a determination is also possible based on the ratio of amplitude levels. What % or more of the amplitude of the first rank was observed as the amplitude may be used as an index. For example, if the amplitude of the second rank is larger than 80% of that of the first rank, the difference may be determined as small; if it is equal to or less than 80%, the difference may be determined as large. An experimentally appropriate value can also be determined for this value.

Step S85 and step S87 indicate levels of reliability as indicated by the result of processing by the determination section 15.

Step S85 indicates that, as a result of determining that the amplitude difference is large at step S84, the reliability is high. There being a large amplitude difference between the first rank and the second rank means that the one P300 waveform was singularly outstanding among all options, which makes it presumable that the P300 waveform was correctly issued. Therefore, this waveform must be highly reliable. In the case of high reliability, the incorrect inference detection step S40 may be set so that any signal pertaining to an incorrect inference is as unlikely to be detected as possible. The determination of presence or absence of a late positive potential at the incorrect inference detection step also employs an electroencephalogram, and thus there is a possibility of mixing of noise. Therefore, adjusting the likeliness with which a late positive potential is detected will provide an improved efficiency of the entire correction apparatus 3.

Therefore, at step S86, the threshold value for the late positive potential detection of the incorrect inference detection step S40 is set high. The threshold value may correspond to, for example, a reference amplitude level for late positive potential detection. When the threshold value is increased, only in the case of a large amplitude will it be determined that a late positive potential is generated. This makes a late positive potential less likely to be detected. Thus, even if a waveform which is similar to a late positive potential is observed due to the influence of slight noise, a late positive potential will not be detected.

Step S87 indicates that, as a result of determining that the amplitude difference is small at step S84, the reliability of P300 detection is low. This is based on the assumption that there is also a high possibility that the option which was actually desired by the user 10 is the option that is regarded as the second rank.

Therefore, at step S88, conversely to step S86, the threshold value for a late positive potential is set low. By making it more likely for a late positive potential to be detected, it is ensured that a late positive potential response at the time of an incorrect inference will not be overlooked as much as possible.

Thus, based on characteristic features of the shapes of event-related potential waveforms stored in the electroencephalogram IF apparatus 2, the reliability of the determination section 15 can be enhanced.

In the present embodiment, an amplitude difference was employed for the reliability determination. However, it will suffice if reliability can be calculated based on information as to whether the first rank and second rank are clearly different or alike among option candidates. For example, a reliability distinction is similarly possible by using a level of similarity in waveforms between the first rank and the second rank, or between the first rank and any other, or by employing a coefficient of correlation with respect to a standard P300 template.

Thus, by also adjusting the threshold value of late positive potential component detection at the determination section 15, the determination at the time of an incorrect inference will become more accurate, thus further enhancing the usability of the interface.

With respect to either one of Embodiments 1 and 2 described above, any process that was described by employing a flowchart can be implemented as a program to be executed by a computer. Such a computer program may be distributed on the market in the form of a product stored on a storage medium, such as a CD-ROM, or transmitted via telecommunication lines such as the Internet. The entire electroencephalogram IF apparatus 2 excluding the output section 14 and the correction apparatus 3 are implemented as a general-purpose processor (semiconductor circuit) executing a computer program. Alternatively, they may be implemented as a special processor in which such a computer program and a processor are integrated.

INDUSTRIAL APPLICABILITY

In a system in which an electroencephalogram interface is used for device control, under various scenes where errors may be present for the selection of a user's desire based on an electroencephalogram, the correction apparatus 3 according to the present invention is broadly applicable to correcting an option, which has been inferred as a candidate, to a new option.

The invention claimed is:

1. A correction apparatus to be incorporated in an electroencephalogram interface system,
the electroencephalogram interface system including:
a biological signal measurement section for measuring and storing an electroencephalogram signal of a user,
an analysis section for analyzing an event-related potential contained in the electroencephalogram signal,
an inference section for inferring an option which is desired by the user based on a result of analysis by the electroencephalogram analysis section, and
an output section for presenting the option inferred by the inference section to the user,
the biological signal measurement section configured for measuring the electroencephalogram signal of the user based on a point of presenting the option to the user as a starting point, wherein,
the correction apparatus comprises a processor device that includes:
a determination section configured to determine correctness of the inferred option based on an event-related potential contained in the electroencephalogram signal acquired after inference of the option; and
a correction section configured to, when the inferred option is determined to be incorrect, correct the inferred option based on the event-related potential which was used for inference of the option, and designate a device operation based on the option after correction.

2. The correction apparatus of claim 1, wherein the determination section determines correctness of the inferred option based on a positive waveform near 600 milliseconds of an event-related potential in the electroencephalogram signal acquired after inference of the option.

3. The correction apparatus of claim 2, wherein,
the determination section retains a threshold value for determining correctness of the option; and
the determination section determines correctness of the inferred option based on whether or not a level of positive amplitude near 600 milliseconds of an event-related potential in the electroencephalogram signal acquired after inference of the option, equal to or greater than the threshold value.

4. The correction apparatus of claim 2, wherein,
the determination section retains a threshold value for determining correctness of the option; and
furthermore the determination section changes the threshold value in accordance with a difference in characteristic features near 300 milliseconds between an event-related potential which is measured corresponding to presentation of the inferred option and an event-related potential which is measured corresponding to presentation of another option, in the electroencephalogram signal which was used for inference of the option.

5. The correction apparatus of claim 4, wherein the determination section changes the predetermined threshold value in accordance with a difference in peak amplitude levels near 300 milliseconds between an event-related potential which is measured corresponding to presentation of the inferred option and an event-related potential which is measured corresponding to presentation of another option.

6. The correction apparatus of claim 5, wherein,
the determination section retains a reference threshold value for determining the difference in peak amplitude levels; and
the determination section gives a greater change in the threshold value for determining correctness of the option if the peak amplitude level is greater than the reference threshold value.

7. The correction apparatus of claim 1, wherein,
the correction section corrects the option by using an event-related potential which is acquired before inference of the option and measured corresponding to presentation of each option.

8. The correction apparatus of claim 7, wherein, before inference of the option,
the output section consecutively presents a plurality of options;
the biological signal measurement section stores an electroencephalogram signal of the user respectively measured based on the presentation of each option as a starting point;
among the event-related potentials in the electroencephalogram signals corresponding to the respective options, the analysis section infers an option corresponding to the event-related potential having a largest amplitude to be the option desired by the user; and
as a correction candidate for the inferred option, the correction section adopts an option corresponding to the event-related potential having a second largest amplitude, among the event-related potentials in the electroencephalogram signals corresponding to the respective options.

9. The correction apparatus of claim 1, wherein the correction section does not modify the inferred option if the determination section determines that the inferred option is correct.

10. A correction method to be executed in an electroencephalogram interface system,
the electroencephalogram interface system performing steps including:
measuring and storing an electroencephalogram signal of a user,
analyzing an event-related potential contained in the electroencephalogram signal,
inferring an option which is desired by the user based on a result of analysis by the electroencephalogram analysis section, and
presenting the option inferred by the inference section to the user,
measuring the electroencephalogram signal of the user based on a point of presenting the option to the user as a starting point, wherein,
the correction method comprises the steps of:
determining correctness of the inferred option based on an event-related potential contained in the electroencephalogram signal acquired after inference of the option;
when the inferred option is determined to be incorrect, correcting the inferred option based on the event-related potential which was used for inference of the option; and
designating a device operation based on the option after correction.

11. A computer program stored on a non-transitory computer-readable medium and executed by a correction apparatus incorporated in an electroencephalogram interface system,
the electroencephalogram interface system including:
a biological signal measurement section for measuring and storing an electroencephalogram signal of a user,
an analysis section for analyzing an event-related potential contained in the electroencephalogram signal,
an inference section for inferring an option which is desired by the user based on a result of analysis by the electroencephalogram analysis section, and
an output section for presenting the option inferred by the inference section to the user,
the biological signal measurement section measuring the electroencephalogram signal of the user based on a point of presenting the option to the user as a starting point, wherein,
the computer program causes a computer of the correction apparatus to execute the steps of:
determining correctness of the inferred option based on an event-related potential contained in the electroencephalogram signal acquired after inference of the option;
when the inferred option is determined to be incorrect, correcting the inferred option based on the event-related potential which was used for inference of the option; and
designating a device operation based on the option after correction.

* * * * *